United States Patent
Kanai et al.

(10) Patent No.: US 9,745,349 B2
(45) Date of Patent: Aug. 29, 2017

(54) CYCLIC PEPTIDE AND PHARMACEUTICAL PRODUCT CONTAINING SAME

(71) Applicant: JAPAN SCIENCE AND TECHNOLOGY AGENCY, Kawaguchi-shi (JP)

(72) Inventors: Motomu Kanai, Bunkyo-ku (JP); Yohei Soma, Bunkyo-ku (JP); Tadamasa Arai, Fujisawa (JP); Daisuke Sasaki, Sumida-ku (JP); Yuki Kobayashi, Toshima-ku (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 14/648,834

(22) PCT Filed: Oct. 18, 2013

(86) PCT No.: PCT/JP2013/078259
§ 371 (c)(1),
(2) Date: Jun. 1, 2015

(87) PCT Pub. No.: WO2014/103481
PCT Pub. Date: Jul. 3, 2014

(65) Prior Publication Data
US 2015/0299262 A1    Oct. 22, 2015

(30) Foreign Application Priority Data

Dec. 27, 2012  (JP) .................................. 2012-284169
Mar. 25, 2013  (JP) .................................. 2013-061722

(51) Int. Cl.
C07K 7/64      (2006.01)
A61K 38/00     (2006.01)
C07K 7/06      (2006.01)

(52) U.S. Cl.
CPC .................. *C07K 7/64* (2013.01); *C07K 7/06* (2013.01); *A61K 38/00* (2013.01)

(58) Field of Classification Search
CPC .................................. C07K 5/12; C07K 5/126
See application file for complete search history.

(56) References Cited

U.S. PATENT DOCUMENTS

| | | | |
|---|---|---|---|
| 5,817,626 A | 10/1998 | Findeis et al. | |
| 5,854,204 A | 12/1998 | Findeis et al. | |
| 5,854,215 A | 12/1998 | Findeis et al. | |
| 6,022,859 A * | 2/2000 | Kiessling | C07K 5/1019 514/17.7 |
| 6,303,567 B1 | 10/2001 | Findeis et al. | |
| 6,319,498 B1 | 11/2001 | Findeis et al. | |
| 6,331,440 B1 | 12/2001 | Nordstedt et al. | |
| 7,060,670 B1 | 6/2006 | Chalifour et al. | |
| 2002/0094957 A1 | 7/2002 | Nordstedt et al. | |
| 2002/0098173 A1 | 7/2002 | Findeis et al. | |
| 2003/0003141 A1 | 1/2003 | Green et al. | |
| 2003/0130484 A1 | 7/2003 | Gordon et al. | |
| 2004/0005307 A1 | 1/2004 | Findeis et al. | |
| 2004/0157781 A1 | 8/2004 | Nordstedt et al. | |
| 2006/0199771 A1 | 9/2006 | Chalifour et al. | |
| 2008/0317834 A1 | 12/2008 | Green et al. | |
| 2009/0264345 A1 * | 10/2009 | McAlpine | C07K 7/64 514/1.1 |
| 2011/0009343 A1 | 1/2011 | Findeis et al. | |

FOREIGN PATENT DOCUMENTS

| | | |
|---|---|---|
| JP | 11-514333 A | 12/1999 |
| JP | 2003-503312 A | 1/2003 |
| JP | 2003-532656 A | 11/2003 |
| WO | 97/21728 A1 | 6/1997 |

(Continued)

OTHER PUBLICATIONS

Al-Obeidi 1989 "Design of a new class of superpotent cyclic .alpha.-melanotropins based on quenched dynamic simulations" J Am Chem Soc 111:3413-3416.*
Aumailley 1991 "Arg-Gly-Asp constrained within cyclic pentapeptides" FEBS 291(1):50-54.*
Fujii 2003 "Molecular-Size reduction of a potent CXCR4-Chemokine antagonist using orthogonal combination of conformation-and sequence-based libraries" Angew Chem 42:3251-3253.*
Rafii 2009 "Recent developments in Alzheimer's disease therapeutics" BMC medicine 7:7.*
Sellers 2010 "Design and synthesis of HSP90 inhibitors: exploring the SAR of sansalvamide A derivatives" Bioorg Med Chem 18(18):6822-6856.*
John Hardy, et al., "The Amyloid Hypothesis of Alzheimer's Disease: Progress and Problems on the Road to Therapeutics", Science, vol. 297, Total 6 Pages, (Jul. 19, 2002).
Stephen A. Gravina, et al., "Amyloid β Protein (Aβ) in Alzheimer's Disease Brain", The Journal of Biological Chemistry, vol. 270, No. 13, pp. 7013-7016, (1995).
Lars O. Tjernberg, et al., "Arrest of β-Amyloid Fibril Formation by a Pentapeptide Ligand", The Journal of Biological Chemistry, vol. 271, No. 15, pp. 8545-8548, (1996).

(Continued)

*Primary Examiner* — Adam M Weidner
(74) *Attorney, Agent, or Firm* — Oblon, McClelland, Maier & Neustadt, L.L.P.

(57) ABSTRACT

A cyclic peptide or a salt thereof of formula (1): X-Leu-Val-$Y^1$-$Y^2$ (1), where X is Lys, Arg, His, Ala, Gly, Ser, or Thr; and $Y^1$ and $Y^2$, which are identical to or different from each other, each represent a group represented by formula (2):

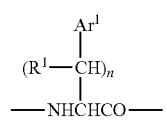

where $Ar^1$ represents an aromatic hydrocarbon group or an aromatic heterocyclic group; $R^1$ represents a hydrogen atom, an alkyl group, a cycloalkyl group, a haloalkyl group, an aromatic hydrocarbon group, or an aromatic heterocyclic group; and n is an integer from 0 to 2. In the cyclic peptide has an α-amino group at the amino terminus of the amino acid sequence which is linked, via a peptide bond, to the carboxyl group at the carboxyl terminus of the amino acid sequence.

4 Claims, No Drawings

(56) References Cited

FOREIGN PATENT DOCUMENTS

WO            02/074931 A2    9/2002
WO   WO 2007/109620 A2    9/2007

OTHER PUBLICATIONS

International Search Report Issued Dec. 10, 2013 in PCT/JP13/078259 Filed Oct. 18, 2013.
Extended European Search Report issued on Jul. 5, 2016 in European Patent Application No. 13868231.5.

* cited by examiner

CYCLIC PEPTIDE AND PHARMACEUTICAL PRODUCT CONTAINING SAME

TECHNICAL FIELD

The present invention relates to a cyclic peptide, and to a preventive or therapeutic drug for a disease associated with amyloid deposition, such as Alzheimer's disease, the drug containing the cyclic peptide.

BACKGROUND ART

Alzheimer's disease is a neurodegenerative disease which is pathologically characterized by formation of senile plaques and neurofibrillary tangle, along with neuronal degeneration and drop out. Alzheimer's disease causes symptoms of dementia; for example, progressive loss of memory, recognition, thinking, and judgment, and eventually leads to death.

Senile plaques deposited in the brain are mainly formed of amyloid-β peptide (Aβ), and this protein is composed of 39 to 43 amino acid residues. Aβ, which exhibits cytotoxicity, is considered to cause Alzheimer's disease (Non-Patent Document 1). Aβ secreted from cells is generally a polypeptide composed of 40 or 42 amino acid residues. In particular, Aβ composed of 42 amino acid residues is known to be deposited in the brain in an early stage with stronger aggregability, and to have strong cytotoxicity (Non-Patent Document 2). Thus, an Aβ aggregation inhibitor is expected to serve as a preventive or therapeutic drug for Alzheimer's disease.

L-[Lys-Leu-Val-Phe-Phe], which is a partial sequence of Aβ, is known to have inhibitory activity for Aβ aggregation (Non-Patent Document 3).

CITATION LIST

Non-Patent Documents

Non-Patent Document 1: J. Hardy, D. J. Selkoe, Science 2002, 297, 353.
Non-Patent Document 2: J. Biol. Chem., 1995, Vol. 270, p 7013
Non-Patent Document 3: J. Biol. Chem., 1996, Vol. 271, p 8545

SUMMARY OF THE INVENTION

Problems to be Solved by the Invention

However, the aforementioned pentapeptide exhibits very weak inhibitory activity for Aβ aggregation. In addition, the pentapeptide, which is composed of natural amino acid residues, exhibits problematically poor metabolic stability.

In view of the foregoing, an object of the present invention is to provide a novel compound which has excellent inhibitory activity for Aβ aggregation, and which is useful as a drug.

Means for Solving the Problems

In order to achieve the aforementioned object, the present inventors have conducted extensive studies focusing on the aforementioned pentapeptide. As a result, the inventors have quite unexpectedly found that a cyclic peptide formed through cyclization of the pentapeptide exhibits inhibitory activity for Aβ aggregation markedly superior to that of the chain peptide. The inventors have also found that a cyclic peptide prepared through substitution of some of the amino acid residues with other amino acid residues exhibits further excellent inhibitory activity for Aβ aggregation, and the cyclic peptide is useful as a preventive or therapeutic drug for various diseases caused by amyloid deposition, such as Alzheimer's disease. The present invention has been accomplished on the basis of these findings.

Accordingly, the present invention provides the following [1] to [17].

[1] A cyclic peptide or a salt thereof, the cyclic peptide having an amino acid sequence represented by the following formula (1):

(wherein X is Lys, Arg, His, Ala, Gly, Ser, or Thr; and $Y^1$ and $Y^2$, which are identical to or different from each other, each represent a group represented by the following formula (2)

(wherein, in formula (2), $Ar^1$ represents an aromatic hydrocarbon group or an aromatic heterocyclic group (the aromatic hydrocarbon group or the aromatic heterocyclic group may have 1 to 5 substituents selected from the group consisting of an alkyl group, a cycloalkyl group, a haloalkyl group, a halogen atom, a hydroxy group, an alkoxy group, an aromatic hydrocarbon group, an aromatic heterocyclic group, and an amino group); $R^1$ represents a hydrogen atom, an alkyl group, a cycloalkyl group, a haloalkyl group, an aromatic hydrocarbon group, or an aromatic heterocyclic group (the aromatic hydrocarbon group or the aromatic heterocyclic group may have 1 to 5 substituents selected from the group consisting of an alkyl group, a cycloalkyl group, a haloalkyl group, a halogen atom, a hydroxy group, an alkoxy group, an aromatic hydrocarbon group, an aromatic heterocyclic group, and an amino group); and n is an integer from 0 to 2)), wherein the α-amino group at the amino terminus of the amino acid sequence is linked, via a peptide bond, to the carboxyl group at the carboxyl terminus of the amino acid sequence.

[2] The cyclic peptide or a salt thereof according to [1], wherein X is Lys or Ala.

[3] The cyclic peptide or a salt thereof according to [1] or [2], wherein the aromatic hydrocarbon group represented by $Ar^1$ or $R^1$ is a C6 to C14 aromatic hydrocarbon group.

[4] The cyclic peptide or a salt thereof according to any of [1] to [3], wherein the aromatic heterocyclic group represented by $Ar^1$ or $R^1$ is an aromatic heterocyclic group having 2 to 9 carbon atoms in total and 1 to 3 heteroatoms selected from the group consisting of nitrogen, oxygen, and sulfur atoms.

[5] The cyclic peptide or a salt thereof according to any of [1] to [4], wherein the aromatic hydrocarbon group represented by $Ar^1$ or $R^1$ is a group selected from the group consisting of a phenyl group, a naphthyl group, and a biphenyl group.

[6] The cyclic peptide or a salt thereof according to any of [1] to [5], wherein the aromatic heterocyclic group represented by $Ar^1$ or $R^1$ is a group selected from the group consisting of a pyrrolyl group, a furanyl group, a thienyl group, an imidazolyl group, an oxazolyl group, a thiazolyl group, a pyridyl group, a pyrimidinyl group, and an indolyl group.

[7] The cyclic peptide or a salt thereof according to any of [1] to [6], wherein the group represented by formula (2) is a group represented by the following formula (2a), (2b), or (2c):

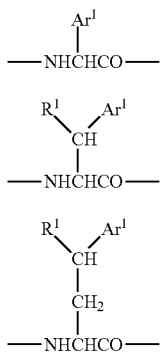

(wherein, in formula (2a), (2b), or (2c), $R^1$ and $Ar^1$ have the same meanings as defined above).

[8] An amyloid-β peptide aggregation inhibitor comprising, as an active ingredient, a cyclic peptide or a salt thereof as recited in any of [1] to [7].

[9] A drug comprising a cyclic peptide or a salt thereof as recited in any of [1] to [7].

[10] The drug according to [9], which is a preventive or therapeutic drug for Alzheimer's disease.

[11] A pharmaceutical composition comprising a cyclic peptide or a salt thereof as recited in any of [1] to [7], and a pharmaceutically acceptable carrier.

[12] The pharmaceutical composition according to [11], which is a pharmaceutical composition for prevention or treatment of Alzheimer's disease.

[13] The cyclic peptide or a salt thereof according to any of [1] to [7] for use in prevention or treatment of a disease.

[14] The cyclic peptide or a salt thereof according to [13], wherein the disease is Alzheimer's disease.

[15] Use of a cyclic peptide or a salt thereof as recited in any of [1] to [7] for producing a drug.

[16] The use according to [15], wherein the drug is for Alzheimer's disease.

[17] A method for preventing or treating Alzheimer's disease, comprising administering a cyclic peptide or a salt thereof as recited in any of [1] to [7] to a subject in need thereof.

Effects of the Invention

The cyclic peptide or a salt thereof having an amino acid sequence represented by formula (1) exhibits very excellent inhibitory activity for Aβ aggregation, and is useful as a preventive or therapeutic drug for diseases caused by amyloid deposition, such as Alzheimer's disease and Down's syndrome.

MODES FOR CARRYING OUT THE INVENTION

The cyclic peptide of the present invention has an amino acid sequence represented by formula (1), wherein the α-amino group at the amino terminus of the amino acid sequence is linked, via a peptide bond, to the carboxyl group at the carboxyl terminus of the amino acid sequence.

The cyclic peptide of the present invention is characterized in that both $Y^1$ and $Y^2$ in formula (1) are aromatic amino acid residues.

In formula (1), X is Lys, Arg, His, Ala, Gly, Ser, or Thr, and preferably Lys or Ala.

In formula (1), $Y^1$ and $Y^2$, which are identical to or different from each other, each represent a group represented by formula (2). In formula (2), $Ar^1$ represents an aromatic hydrocarbon group or an aromatic heterocyclic group (the aromatic hydrocarbon group or the aromatic heterocyclic group may have 1 to 5 substituents selected from the group consisting of an alkyl group, a cycloalkyl group, a haloalkyl group, a halogen atom, a hydroxy group, an alkoxy group, an aromatic hydrocarbon group, an aromatic heterocyclic group, and an amino group). $R^1$ represents a hydrogen atom, an alkyl group, a cycloalkyl group, a haloalkyl group, an aromatic hydrocarbon group, or an aromatic heterocyclic group (the aromatic hydrocarbon group or the aromatic heterocyclic group may have 1 to 5 substituents selected from the group consisting of an alkyl group, a cycloalkyl group, a haloalkyl group, a halogen atom, a hydroxy group, an alkoxy group, an aromatic hydrocarbon group, an aromatic heterocyclic group, and an amino group).

The aromatic hydrocarbon group represented by $Ar^1$ or $R^1$ is, for example, a C6 to C14 aromatic hydrocarbon group, and is preferably a C6 to C12 aromatic hydrocarbon group. Specific examples of the aromatic hydrocarbon group include a phenyl group, an indenyl group, a naphthyl group, and a biphenyl group. More preferred are a phenyl group, a naphthyl group, and a biphenyl group. The aromatic hydrocarbon groups represented by $Ar^1$ and $R^1$ may be identical to or different from each other.

The aromatic heterocyclic group represented by $Ar^1$ or $R^1$ is, for example, an aromatic heterocyclic group having 1 to 3 heteroatoms selected from the group consisting of nitrogen, oxygen, and sulfur atoms, and is preferably an aromatic heterocyclic group having 2 to 9 carbon atoms in total and 1 to 3 heteroatoms selected from the group consisting of nitrogen, oxygen, and sulfur atoms. Specific examples of the aromatic heterocyclic group include a pyrrolyl group, a furanyl group, a thienyl group, an imidazolyl group, an oxazolyl group, a thiazolyl group, a triazinyl group, a pyridyl group, a pyrimidinyl group, an indolyl group, and a benzimidazolyl group. Preferred are a pyrrolyl group, a furanyl group, a thienyl group, an imidazolyl group, an oxazolyl group, a thiazolyl group, a pyridyl group, a pyrimidinyl group, and an indolyl group. More referred are an imidazolyl group and a pyridyl group. The aromatic heterocyclic groups represented by $Ar^1$ and $R^1$ may be identical to or different from each other.

The aforementioned aromatic hydrocarbon group or aromatic heterocyclic group may have 1 to 5 substituents selected from the group consisting of an alkyl group, a cycloalkyl group, a haloalkyl group, a halogen atom, a hydroxy group, an alkoxy group, an aromatic hydrocarbon group, an aromatic heterocyclic group, and an amino group. The alkyl group is, for example, a C1 to C6 alkyl group, and is preferably a C1 to C4 alkyl group. Specific examples of the alkyl group include a methyl group, an ethyl group, an n-propyl group, an isopropyl group, an n-butyl group, an isobutyl group, a sec-butyl group, and a tert-butyl group. The cycloalkyl group is, for example, a C3 to C8 cycloalkyl group. The C3 to C8 cycloalkyl group, which refers to a C3 to C8 monovalent cyclic saturated hydrocarbon group formed of carbon and hydrogen atoms, is preferably a C3 to C6 cycloalkyl group. Specific examples of the cycloalkyl group include a cyclopropyl group, a cyclobutyl group, a cyclopentyl group, and a cyclohexyl group. The haloalkyl group, which refers to a C1 to C6 alkyl group having at least one halogen atom substituted for any hydrogen atom(s), is preferably a C1 to C4 haloalkyl group. Specific examples of the haloalkyl group include a fluoromethyl group, a difluoromethyl group, a dichloromethyl group, a trifluoromethyl group, a trichloromethyl group, a 2,2,2-trifluoroethyl group, and a 2,2,2-trichloroethyl group. Examples of the halogen atom include a fluorine atom, a chlorine atom, a bromine atom, and an iodine atom. The alkoxy group is, for example, a C1 to C6 alkoxy group, and is preferably a C1 to C4 alkoxy group. Specific examples of the alkoxy group include a methoxy group, an ethoxy group, a propyloxy group, and an isopropyloxy group. The aromatic hydrocarbon group is, for example, a C6 to C14 aromatic hydrocarbon group, and is preferably a C6 to C12 aromatic hydrocarbon group. Specific examples of the aromatic hydrocarbon group include a phenyl group, an indenyl group, a naphthyl group, and a biphenyl group. More preferred are a phenyl group, a naphthyl group, and a biphenyl group. The aromatic heterocyclic group is, for example, an aromatic heterocyclic group having 1 to 3 heteroatoms selected from the group consisting of nitrogen, oxygen, and sulfur atoms, and is preferably an aromatic heterocyclic group having 2 to 9 carbon atoms in total and 1 to 3 heteroatoms selected from the group consisting of nitrogen, oxygen, and sulfur atoms. Specific examples of the aromatic heterocyclic group include a pyrrolyl group, a furanyl group, a thienyl group, an imidazolyl group, an oxazolyl group, a thiazolyl group, a triazinyl group, a pyridyl group, a pyrimidinyl group, an indolyl group, and a benzimidazolyl group. Preferred are a pyrrolyl group, a furanyl group, a thienyl group, an imidazolyl group, an oxazolyl group, a thiazolyl group, a pyridyl group, a pyrimidinyl group, and an indolyl group. More referred are an imidazolyl group and a pyridyl group. The number of such substituents on the aforementioned aromatic hydrocarbon group or aromatic heterocyclic group may be 1 to 5, but is preferably 1 or 2.

Specific examples of preferred aromatic hydrocarbon and aromatic heterocyclic groups represented by $Ar^1$ or $R^1$ include a phenyl group, a naphthyl group, a halogenophenyl group such as 4-fluorophenyl, a hydroxyphenyl group, an aminophenyl group, a $C_{1-6}$ alkyl-phenyl group, a $C_{3-8}$ cycloalkyl-phenyl group, a $C_{1-4}$ haloalkyl-phenyl group, a $C_{1-4}$ alkoxy-phenyl group, biphenyl groups such as biphenyl-4-yl, biphenyl-3-yl, and biphenyl-2-yl, a hydroxybiphenyl group such as 3'-hydroxybiphenyl, a pyridyl-phenyl group, a pyrimidinyl-phenyl group, a pyridyl group, a pyrrolyl group, a furanyl group, a thienyl group, an imidazolyl group, an oxazolyl group, a thiazolyl group, and an indolyl group.

The alkyl group represented by $R^1$ is, for example, a C1 to C6 alkyl group, and is preferably a C1 to C4 alkyl group. Specific examples of the alkyl group include a methyl group, an ethyl group, an n-propyl group, an isopropyl group, an n-butyl group, an isobutyl group, a sec-butyl group, and a tert-butyl group. The cycloalkyl group is, for example, a C3 to C8 cycloalkyl group, and is preferably a C3 to C6 cycloalkyl group. Examples thereof include a cyclopropyl group, a cyclobutyl group, a cyclopentyl group, and a cyclohexyl group. The haloalkyl group is, for example, a C1 to C6 haloalkyl group, and is preferably a C1 to C4 haloalkyl group. Examples thereof include a fluoromethyl group, a difluoromethyl group, a dichloromethyl group, a trifluoromethyl group, a trichloromethyl group, a 2,2,2-trifluoroethyl group, a trichloromethyl group, a 2,2,2-trifluoroethyl group, and a 2,2,2-trichloroethyl group. The alkoxy group is, for example, a C1 to C6 alkoxy group. Examples thereof include a methoxy group, an ethoxy group, and an isopropyloxy group.

$R^1$ is more preferably a hydrogen atom, the aforementioned aromatic hydrocarbon group, or the aforementioned aromatic heterocyclic group.

In formula (2), n is an integer from 0 to 2, and is more preferably 1.

The group represented by formula (2) is preferably, for example, a group represented by the following formula (2a), (2b), or (2c):

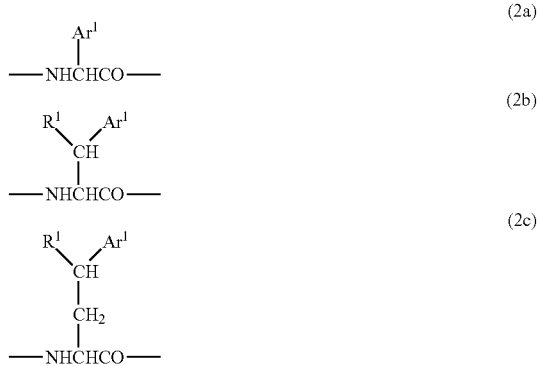

(wherein, in formula (2a), (2b), or (2c), $R^1$ and $Ar^1$ have the same meanings as defined above). $R^1$ in formula (2b) or (2c) is preferably a hydrogen atom, the aforementioned aromatic hydrocarbon group, or the aforementioned aromatic heterocyclic group. Specific examples of the aromatic hydrocarbon group and aromatic heterocyclic group represented by $R^1$ or $Ar^1$ include a phenyl group, a naphthyl group, a halogenophenyl group such as a 4-fluorophenyl group, a hydroxyphenyl group, an aminophenyl group, a $C_{1-6}$ alkyl-phenyl group, a $C_{3-8}$ cycloalkyl-phenyl group, a $C_{1-4}$ haloalkyl-phenyl group, a $C_{1-4}$ alkoxy-phenyl group, biphenyl groups such as biphenyl-4-yl, biphenyl-3-yl, and biphenyl-2-yl groups, a hydroxybiphenyl group such as a 3'-hydroxybiphenyl group, a pyridyl group, an imidazolyl group, a pyridyl-phenyl group, and a pyrimidinyl-phenyl group.

The cyclic peptide of formula (1) is more preferably a cyclic peptide having an amino acid sequence represented by the following formula (1a), wherein the α-amino group at the amino terminus of the amino acid sequence is linked, via a peptide bond, to the carboxyl group at the carboxyl terminus of the amino acid sequence.

(wherein, in formula (1a), X and $Y^1$ have the same meanings as defined above).

In formula (1a), X is preferably Lys or Ala, and $Y^1$ is preferably a group represented by formula (2a), (2b), or (2c).

Each of the amino acid residues in formula (1) may be in L-form or D-form. D-form is preferred from the viewpoint of metabolic stability. Examples of the salt of the cyclic peptide of formula (1) include acid addition salts; for example, inorganic acid salts, such as hydrochloride, sulfate, nitrate, carbonate, and phosphate; and organic acid salts such as acetate, oxalate, and succinate.

Specific examples of preferred cyclic peptides of formula (1) will now be described. In the below-described formulas, "Ph" denotes a phenyl group, "F-Ph" a fluorophenyl group, "bi-Ph" a biphenyl group, "Py" a pyridyl group, "Pheth" a phenylethyl group, and "Nal" a naphthylalanyl group.

cyclo-L-[Lys-Leu-Val-Phe-Phe] (SEQ ID NO: 1)

cyclo-D-[Lys-Leu-Val-Phe-Phe] (SEQ ID NO: 1)

cyclo-D-[Ala-Leu-Val-Phe-Phe] (SEQ ID NO: 2)

cyclo-D-[Lys-Leu-Val-Phe(βPh)-Phe] (SEQ ID NO: 3)

cyclo-D-[Lys-Leu-Val-(β,β-FPh)Ala-Phe] (SEQ ID NO: 4)

cyclo-D-[Lys-Leu-Val-(β,β-Py)Ala-Phe] (SEQ ID NO: 5)

cyclo-D-[Lys-Leu-Val-(4-bi-Ph)Ala-Phe] (SEQ ID NO: 6)

cyclo-D-[Lys-Leu-Val-(3-bi-Ph)Ala-Phe] (SEQ ID NO: 7)

cyclo-D-[Lys-Leu-Val-(2-bi-Ph)Ala-Phe] (SEQ ID NO: 8)

cyclo-D-[Lys-Leu-Val-(1-Nal)-Phe] (SEQ ID NO: 9)

cyclo-D-[Lys-Leu-Val-(β-Py)Ala-Phe] (SEQ ID NO: 10)

cyclo-D-[Lys-Leu-Val-(4-(2-Py)-Ph)Ala-Phe] (SEQ ID NO: 11)

cyclo-D-[Lys-Leu-Val-(Ph)Gly-Phe] (SEQ ID NO: 12)

cyclo-D-[Lys-Leu-Val-(Pheth)Gly-Phe] (SEQ ID NO: 13)

cyclo-D-[Lys-Leu-Val-(4-OH)Phe-Phe] (SEQ ID NO: 14)

cyclo-D-[Lys-Leu-Val-(4-NH$_2$)Phe-Phe] (SEQ ID NO: 15)

cyclo-D-[Lys-Leu-Val-(4-(2-Py)-Ph)Ala-Phe] (SEQ ID NO: 20)

cyclo-D-[Lys-Leu-Val-(4-(3-Py)-Ph)Ala-Phe] (SEQ ID NO: 21)

cyclo-D-[Lys-Leu-Val-(4-(4-Py)-Ph)Ala-Phe] (SEQ ID NO: 22)

cyclo-D-[Lys-Leu-Val-(4-(5-pyrimidine)-Ph)Ala-Phe] (SEQ ID NO: 23)

cyclo-D-[Lys-Leu-Val-(4-(3-hydroxyphenyl)-Ph)Ala-Phe] (SEQ ID NO: 24)

The cyclic peptide (1) of the present invention can be produced through a common organic-chemical peptide synthesis process. The organic-chemical peptide synthesis process involves protection of a functional group, activation of a carboxyl group, formation of a peptide bond, and removal of a protecting group, which are generally employed in the art.

As described in the Examples hereinbelow, the cyclic peptide of the present invention or a salt thereof exhibits strong inhibitory activity for Aβ aggregation and high metabolic stability. Thus, the cyclic peptide or a salt thereof is useful as an Aβ aggregation inhibitor, and also as a preventive or therapeutic drug for diseases associated with amyloid deposition or Aβ aggregation in animals (including human), such as Alzheimer's disease and Down's syndrome.

When the cyclic peptide of the present invention is used as a drug for humans, the daily dose for an adult is 1 mg to 1 g, preferably 10 mg to 300 mg.

A pharmaceutical composition containing the cyclic peptide falling within the scope of the present invention may be prepared through any drug preparation method by selecting a suitable drug form in consideration of the manner of administration, and using a pharmaceutically acceptable carrier. Examples of the form of the pharmaceutical composition, which contains the cyclic peptide of the present invention as a main component, include oral preparations, such as tablets, powders, granules, capsules, solutions, syrups, elixirs, and oil or aqueous suspensions.

Injection preparations may contain a stabilizer, a preservative, or a solubilizing agent. Alternatively, a solution which may contain any of these additives may be placed in a container and converted into solid through, for example, freeze-drying, and the thus-prepared solid preparation may be reconstituted before use. In connection therewith, a single dose or a plurality of doses may be contained into one container.

Exemplary external application forms include solutions, suspensions, emulsions, ointments, gels, creams, lotions, sprays, and patches.

Solid preparations may contain pharmaceutically acceptable additives along with the cyclic peptide of the present invention. For production of such a solid preparation, the cyclic peptide may be mixed with an optionally selected additive, such as a filler, an extender, a binder, a disintegrator, a dissolution promoter, a humectant, or a lubricant.

Exemplary liquid preparations include solutions, suspensions, and emulsions. Such a preparation may contain an additive such as a suspending agent or an emulsifier.

EXAMPLES

The present invention will next be described in detail by way of examples, which should not be construed as limiting the invention thereto.

Production Example 1

A 2-chlorotrityl chloride resin (400 mg), Fmoc-Phe-OH (232.4 mg, 0.6 mmol), 1,2-dichloroethane (3 mL), and N,N-diisopropylethylamine (420 μL, 2.4 mmol) were sequentially added to a reaction vessel, and reaction was allowed to proceed for one hour. The reaction mixture was washed with DMF, and methanol (400 μL) and N,N-diisopropylethylamine (278 μL, 1.5 mmol) were then added to the mixture, followed by shaking for 20 minutes. The mixture was thoroughly washed with DMF, DMF-H$_2$O (1:1), and methanol, and the resin was then dried with a vacuum pump. The percent amino acid substitution was determined from the amount of an Fmoc luminophore cleaved through piperidine treatment (0.33 mmol).

Fmoc amino acid (0.085 mmol) was condensed with the resultant Fmoc-Phe-O-resin (0.034 mmol) in the presence of N,N'-diisopropylcarbodiimide (13.2 μL, 0.085 mmol) and 1-hydroxybenzotriazole (13.0 mg, 0.085 mmol), and the Fmoc group was subsequently removed with 20% piperidine/DMF. This cycle was repeated to form a protected peptide resin. The entirety of the resultant protected peptide resin was stirred in triisopropylsilane-H$_2$O-trifluoroacetic acid (2.5:2.5:95) for 60 minutes, followed by concentration and reprecipitation with $Et_2O$, to thereby produce a white solid (5.8 mg). This crude peptide was stirred in DMF (13 mL) for 15 hours in the presence of O-(7-azabenzotriazol-1-yl)-N,N,N',N'-tetramethyluronium hexafluorophosphate (HATU, 5.0 mg, 1.3 μmol) and N,N-diisopropylethylamine (4.6 μL, 2.6 μmol). The reaction mixture was mixed with water, and the mixture was subjected to extraction with ethyl acetate. The extract was washed with brine, dried over sodium sulfate, and then concentrated. The resultant residue was mixed with 20% piperidine/DMF (2 mL), and the mixture was stirred at room temperature for five hours. The reaction mixture was mixed with water, and the mixture was subjected to extraction with ethyl acetate. The extract was washed with brine, dried over sodium sulfate, and then concentrated. The resultant residue was purified through preparative scale HPLC (0.1% aqueous TFA-$CH_3CN$ system). The purified product was lyophilized to produce a white amorphous compound 1 (cyclo-L-[Lys-Leu-Val-Phe-Phe]) (0.31 mg).

Yield: 1.4%; MALDI-MS (TOF): $M_{calc}$ 634.3; $M+H_{found}$: 635.1; retention time in reversed-phase ODS column: 24.1 min (column: YMC-Pack ODS-AM (4.6×150 mm), 0-100% $CH_3CN$ in 0.1% aqueous TFA).

Production Example 2 (Compound 2:
cyclo-D-[Lys-Leu-Val-Phe-Phe])

Compound 2 was synthesized in a manner similar to that employed for compound 1. Yield: 5.2%; MALDI-MS (TOF): $M_{calc}$: 634.3; $M+H_{found}$: 635.4; retention time in reversed-phase ODS column=24.1 min (column: YMC-Pack ODS-AM (4.6×150 mm), 0-100% $CH_3CN$ in 0.1% aqueous TFA).

Production Example 3 (Compound 3:
cyclo-D-[Ala-Leu-Val-Phe-Phe])

Compound 3 was synthesized in a manner similar to that employed for compound 1. Yield: 1.3%; MALDI-MS (TOF): $M_{calc}$: 577.3; $M+H_{found}$: 578.2; retention time in reversed-phase ODS column=27.1 min (column: YMC-Pack ODS-AM (4.6×150 mm), 0-100% $CH_3CN$ in 0.1% aqueous TFA).

Production Example 4 (Compound 4:
cyclo-D-[Lys-Ala-Val-Phe-Phe])

Compound 4 was synthesized in a manner similar to that employed for compound 1. Yield: 1.8%; MALDI-MS (TOF): $M_{calc}$: 592.3; $M+H_{found}$: 593.1; retention time in reversed-phase ODS column=21.4 min (column: YMC-Pack ODS-AM (4.6×150 mm), 0-100% $CH_3CN$ in 0.1% aqueous TFA).

Production Example 5 (Compound 5:
cyclo-D-[Lys-Leu-Ala-Phe-Phe])

Compound 5 was synthesized in a manner similar to that employed for compound 1. Yield: 2.5%; MALDI-MS (TOF): $M_{calc}$: 606.4; $M+H_{found}$: 607.1; retention time in reversed-phase ODS column=21.5 min (column: YMC-Pack ODS-AM (4.6×150 mm), 0-100% $CH_3CN$ in 0.1% aqueous TFA).

Production Example 6 (Compound 6:
cyclo-D-[Lys-Leu-Val-Ala-Phe])

Compound 6 was synthesized in a manner similar to that employed for compound 1. Yield: 0.4%; MALDI-MS (TOF): $M_{calc}$: 558.4; $M+H_{found}$: 558.7; retention time in reversed-phase ODS column=19.8 min (column: YMC-Pack ODS-AM (4.6×150 mm), 0-100% $CH_3CN$ in 0.1% aqueous TFA).

Production Example 7 (Compound 7:
cyclo-D-[Lys-Leu-Val-Phe-Ala])

Compound 7 was synthesized in a manner similar to that employed for compound 1. Yield: 2.2%; MALDI-MS (TOF): $M_{calc}$: 558.4; $M+H_{found}$: 558.7; retention time in reversed-phase ODS column=20.9 min (column: YMC-Pack ODS-AM (4.6×150 mm), 0-100% $CH_3CN$ in 0.1% aqueous TFA).

Production Example 8 (Compound 8:
cyclo-D-[Lys-Leu-Val-Phe(βPh)-Phe])

Compound 8 was synthesized in a manner similar to that employed for compound 1. Yield: 10.9%; MALDI-MS (TOF): $M_{calc}$: 710.4; $M+H_{found}$: 711.4; retention time in reversed-phase ODS column=25.8 min (column: YMC-Pack ODS-AM (4.6×150 mm), 0-100% $CH_3CN$ in 0.1% aqueous TFA).

Production Example 9 (Compound 9: cyclo-D-[Lys-Leu-Val-(4-bi-Ph)Ala-Phe])

Compound 9 was synthesized in a manner similar to that employed for compound 1. Yield: 1.9%; MALDI-MS (TOF): $M_{calc}$: 710.4; $M+H_{found}$: 711.3; retention time in reversed-phase ODS column=27.0 min (column: YMC-Pack ODS-AM (4.6×150 mm), 0-100% $CH_3CN$ in 0.1% aqueous TFA).

Production Example 10 (Compound 10: cyclo-D-[Lys-Leu-Val-(3-bi-Ph)Ala-Phe])

Compound 10 was synthesized in a manner similar to that employed for compound 1. Yield: 2.7%; MALDI-MS (TOF): $M_{calc}$: 710.4; $M+H_{found}$: 711.3; retention time in reversed-phase ODS column=26.9 min (column: YMC-Pack ODS-AM (4.6×150 mm), 0-100% $CH_3CN$ in 0.1% aqueous TFA).

Production Example 11 (Compound 11: cyclo-D-[Lys-Leu-Val-(2-bi-Ph)Ala-Phe])

Compound 11 was synthesized in a manner similar to that employed for compound 1. Yield: 3.0%; MALDI-MS (TOF): $M_{calc}$: 710.4; $M+H_{found}$: 711.2; retention time in reversed-phase ODS column=26.5 min (column: YMC-Pack ODS-AM (4.6×150 mm), 0-100% $CH_3CN$ in 0.1% aqueous TFA).

Production Example 12 (Compound 12: cyclo-D-[Lys-Leu-Val-(1-Nal)-Phe])

Compound 12 was synthesized in a manner similar to that employed for compound 1. Yield: 21%; MALDI-MS (TOF): $M_{calc}$: 684.4; $M+Na_{found}$: 707.5; retention time in reversed-phase ODS column=25.9 min (column: YMC-Pack ODS-AM (4.6×150 mm), 0-100% $CH_3CN$ in 0.1% aqueous TFA).

Production Example 13 (Compound 13: cyclo-D-[Lys-Leu-Val-(4-(2-Py)-Ph)Ala-Phe])

Compound 13 was synthesized in a manner similar to that employed for compound 1. Yield: 2.2%; MALDI-MS (TOF): M$_{calc}$: 711.4; M+H$_{found}$: 712.1; retention time in reversed-phase ODS column=19.9 min (column: YMC-Pack ODS-AM (4.6×150 mm), 0-100% CH$_3$CN in 0.1% aqueous TFA).

Production Example 14 (Compound 14: cyclo-D-[Lys-Leu-Val-(4-(3-Py)-Ph)Ala-Phe])

Compound 14 was synthesized in a manner similar to that employed for compound 1. Yield: 1.3%; MALDI-MS (TOF): M$_{calc}$: 711.4; M+H$_{found}$: 712.1; retention time in reversed-phase ODS column=19.8 min (column: YMC-Pack ODS-AM (4.6×150 mm), 0-100% CH$_3$CN in 0.1% aqueous TFA).

Production Example 15 (Compound 15: cyclo-D-[Lys-Leu-Val-(4-(4-Py)-Ph)Ala-Phe])

Compound 15 was synthesized in a manner similar to that employed for compound 1. Yield: 2.2%; MALDI-MS (TOF): M$_{calc}$: 711.4; M+H$_{found}$: 712.3; retention time in reversed-phase ODS column=19.7 min (column: YMC-Pack ODS-AM (4.6×150 mm), 0-100% CH$_3$CN in 0.1% aqueous TFA).

Production Example 16 (Compound 16: cyclo-D-[Lys-Leu-Val-(4-(5-pyrimidine)-Ph)Ala-Phe])

Compound 16 was synthesized in a manner similar to that employed for compound 1. Yield: 0.4%; MALDI-MS (TOF): M$_{calc}$: 712.4; M+H$_{found}$: 713.6; retention time in reversed-phase ODS column=22.5 min (column: YMC-Pack ODS-AM (4.6×150 mm), 0-100% CH$_3$CN in 0.1% aqueous TFA).

Production Example 17 (Compound 17: cyclo-D-[Lys-Leu-Val-(4-(3-phenol)-Ph)Ala-Phe])

Compound 17 was synthesized in a manner similar to that employed for compound 1. Yield: 1.6%; MALDI-MS (TOF): M$_{calc}$: 726.4; M+H$_{found}$: 727.5; retention time in reversed-phase ODS column=24.0 min (column: YMC-Pack ODS-AM (4.6×150 mm), 0-100% CH$_3$CN in 0.1% aqueous TFA).

Test Example 1 (Aβ Aggregation Inhibition Test)

An aggregation inhibitory peptide solution (DMSO solution) was added to a 0.1 M phosphate buffer (pH 7.4, 50 μL) containing O-acyl isopeptide of Aβ (10 μM) (final concentration of inhibitor: 30 μM, 1% DMSO), and the resultant mixture was incubated at 37° C. for a specific period of time. Thereafter, a portion of the reaction mixture (10 μL) was added to a mixture of thioflavin T solution (50 μM thioflavin T, 10 μL) and 50 mM glycine-NaOH buffer (pH 8.5, 396 μL). Immediately thereafter, they were mixed together, and the fluorescence intensity of thioflavin T was measured at an excitation wavelength of 440 nm and an emission wavelength of 480 nm.

Table 1 shows the results; i.e., the ratio of aggregation inhibitory activity to the aggregation inhibitory activity (taken as 100) of DMSO solution (control).

TABLE 1

| Compound | Structure | Aggregation inhibitory activity ratio (the lower the ratio, the higher the inhibitory activity) |
|---|---|---|
| Control | DMSO (control) | 100 |
| Chain compound (known) | L-[Lys-Leu-Val-Phe-Phe] (SEQ ID NO: 1) | 107 |
| 1 | cyclo-L-[Lys-Leu-Val-Phe-Phe] (SEQ ID NO: 1) | 63 |
| 2 | cyclo-D-[Lys-Leu-Val-Phe-Phe] (SEQ ID NO: 1) | 65 |
| 3 | cyclo-D-[Ala-Leu-Val-Phe-Phe] (SEQ ID NO: 2) | 66 |
| 4 | cyclo-D-[Lys-Ala-Val-Phe-Phe] (SEQ ID NO: 15) | 88 |
| 5 | cyclo-D-[Lys-Leu-Ala-Phe-Phe] (SEQ ID NO: 16) | 82 |
| 6 | cyclo-D-[Lys-Leu-Val-Ala-Phe] (SEQ ID NO: 17) | 106 |
| 7 | cyclo-D-[Lys-Leu-Val-Phe-Ala] (SEQ ID NO: 18) | 104 |
| 8 | cyclo-D-[Lys-Leu-Val-Phe(βPh)-Phe] (SEQ ID NO: 3) | 28 |
| 9 | cyclo-D-[Lys-Leu-Val-(4-bi-Ph)Ala-Phe] (SEQ ID NO: 6) | 21 |
| 10 | cyclo-D-[Lys-Leu-Val-(3-bi-Ph)Ala-Phe] (SEQ ID NO: 7) | 23 |
| 11 | cyclo-D-[Lys-Leu-Val-(2-bi-Ph)Ala-Phe] (SEQ ID NO: 8) | 19 |
| 12 | cyclo-D-[Lys-Leu-Val-(1-Nal)-Phe] (SEQ ID NO: 9) | 13 |
| 13 | cyclo-D-[Lys-Leu-Val-(4-(2-Py)-Ph)Ala-Phe] (SEQ ID NO: 20) | 81 |
| 14 | cyclo-D-[Lys-Leu-Val-(4-(3-Py)-Ph)Ala-Phe] (SEQ ID NO: 21) | 49 |

TABLE 1-continued

| Compound | Structure | Aggregation inhibitory activity ratio (the lower the ratio, the higher the inhibitory activity) |
|---|---|---|
| 15 | cyclo-D-[Lys-Leu-Val-(4-(4-Py)-Ph)Ala-Phe] (SEQ ID NO: 22) | 57 |
| 16 | cyclo-D-[Lys-Leu-Val-(4-(5-pyrimidine)-Ph)Ala-Phe] (SEQ ID NO: 23) | 90 |
| 17 | cyclo-D-[Lys-Leu-Val-(4-(3-hydroxyphenyl)-Ph)Ala-Phe] (SEQ ID NO: 24) | 39 |

The test results indicate that compounds 1, 2, 3, and 8 to 17 exhibit Aβ aggregation inhibitory activity higher than that of the chain compound. In particular, compounds 8 to 12 exhibit markedly high Aβ aggregation inhibitory activity.

The invention claimed is:

1. A cyclic peptide or a salt thereof, the cyclic peptide having an amino acid sequence represented by a formula (1):

$$X\text{-Leu-Val-}Y^1\text{-}Y^2 \quad (1)$$

wherein X is Lys or Ala; and $Y^2$ is Phe and $Y^1$ is a group of represented by formula (2b):

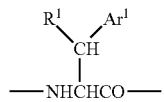

(2b)

wherein, in formula (2b), $Ar^1$ represents a $C_6$ to $C_{14}$ aromatic hydrocarbon group, optionally having 1 to 5 substituents selected from the group consisting of a $C_{1-6}$ alkyl group, a $C_{1-6}$ haloalkyl group, a halogen atom, $C_{1-6}$ alkoxy group, a hydroxy group, 3-pyridyl group and 4-pyridyl group; and $R^1$ represents a hydrogen atom or a phenyl group, wherein the α-amino group at the amino terminus of the amino acid sequence is linked, via a peptide bond, to the carboxyl group at the carboxyl terminus of the amino acid sequence.

2. The cyclic peptide or salt thereof according to claim 1, wherein $Ar^1$ is the $C_6$ to $C_{14}$ aromatic hydrocarbon group and is selected from the group consisting of a phenyl group, a naphthyl group, a halogenophenyl group, a hydroxyphenyl group, a $C_{1-6}$ alkyl-phenyl group, a $C_{1-6}$ haloalkyl-phenyl group, a $C_{1-6}$ alkoxy-phenyl group, a biphenyl group, a hydroxybiphenyl group, and a pyridyl-phenyl group.

3. A pharmaceutical composition comprising the cyclic peptide or salt thereof according to claim 1, and a pharmaceutically acceptable carrier.

4. A method for treating Alzheimer's disease, comprising administering the cyclic peptide or salt thereof according to claim 1 to a subject in need thereof.

\* \* \* \* \*

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial sequence
<220> FEATURE:
<223> OTHER INFORMATION: cyclopeptide

<400> SEQUENCE: 1

Lys Leu Val Phe Phe
1               5

<210> SEQ ID NO 2
<211> LENGTH: 5
<212> TYPE: PRT
<213> ORGANISM: Artificial sequence
<220> FEATURE:
<223> OTHER INFORMATION: cyclopeptide

<400> SEQUENCE: 2

Ala Leu Val Phe Phe
1               5

<210> SEQ ID NO 3
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is beta-phenyl phenylalanine

<400> SEQUENCE: 3

Lys Leu Val Xaa Phe
1               5

<210> SEQ ID NO 4
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is beta,beta-di(4-fluorophenyl)alanine
```

```
<400> SEQUENCE: 4

Lys Leu Val Xaa Phe
1               5

<210> SEQ ID NO 5
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is beta,beta-di(2-pyridyl)alanine

<400> SEQUENCE: 5

Lys Leu Val Xaa Phe
1               5

<210> SEQ ID NO 6
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-biphenylalanine

<400> SEQUENCE: 6

Lys Leu Val Xaa Phe
1               5

<210> SEQ ID NO 7
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 3-biphenylalanine

<400> SEQUENCE: 7

Lys Leu Val Xaa Phe
1               5

<210> SEQ ID NO 8
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 2-biphenylalanine

<400> SEQUENCE: 8

Lys Leu Val Xaa Phe
1               5

<210> SEQ ID NO 9
<211> LENGTH: 5
<212> TYPE: PRT
<213> ORGANISM: Artificial sequence
<220> FEATURE:
```

```
<223> OTHER INFORMATION: cyclopeptide
<220> FEATURE:
<221> NAME/KEY: misc_feature
<222> LOCATION: (4)..(4)
<223> OTHER INFORMATION: Xaa is 1-naphthylalanine

<400> SEQUENCE: 9

Lys Leu Val Xaa Phe
1               5

<210> SEQ ID NO 10
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is beta-pyridylalanine

<400> SEQUENCE: 10

Lys Leu Val Xaa Phe
1               5

<210> SEQ ID NO 11
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is (4-(2-pyridyl)phenyl)alanine

<400> SEQUENCE: 11

Lys Leu Val Xaa Phe
1               5

<210> SEQ ID NO 12
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is phenylglycine

<400> SEQUENCE: 12

Lys Leu Val Xaa Phe
1               5

<210> SEQ ID NO 13
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is phenylethyl glycine

<400> SEQUENCE: 13

Lys Leu Val Xaa Phe
1               5
```

```
<210> SEQ ID NO 14
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-hydroxyphenyl phenylalanine

<400> SEQUENCE: 14

Lys Leu Val Xaa Phe
1               5

<210> SEQ ID NO 15
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-aminophenyl phenylalanine

<400> SEQUENCE: 15

Lys Leu Val Xaa Phe
1               5

<210> SEQ ID NO 16
<211> LENGTH: 5
<212> TYPE: PRT
<213> ORGANISM: Artificial sequence
<220> FEATURE:
<223> OTHER INFORMATION: cyclopeptide

<400> SEQUENCE: 16

Lys Ala Val Phe Phe
1               5

<210> SEQ ID NO 17
<211> LENGTH: 5
<212> TYPE: PRT
<213> ORGANISM: Artificial sequence
<220> FEATURE:
<223> OTHER INFORMATION: cyclopeptide

<400> SEQUENCE: 17

Lys Leu Ala Phe Phe
1               5

<210> SEQ ID NO 18
<211> LENGTH: 5
<212> TYPE: PRT
<213> ORGANISM: Artificial sequence
<220> FEATURE:
<223> OTHER INFORMATION: cyclopeptide

<400> SEQUENCE: 18

Lys Leu Val Ala Phe
1               5

<210> SEQ ID NO 19
<211> LENGTH: 5
<212> TYPE: PRT
<213> ORGANISM: Artificial sequence
<220> FEATURE:
```

```
<223> OTHER INFORMATION: cyclopeptide

<400> SEQUENCE: 19

Lys Leu Val Phe Ala
1               5

<210> SEQ ID NO 20
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-(2-pyridyl) phenylalanine

<400> SEQUENCE: 20

Lys Leu Val Xaa Phe
1               5

<210> SEQ ID NO 21
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-(3-pyridyl) phenylalanine

<400> SEQUENCE: 21

Lys Leu Val Xaa Phe
1               5

<210> SEQ ID NO 22
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-(4-pyridyl) phenylalanine

<400> SEQUENCE: 22

Lys Leu Val Xaa Phe
1               5

<210> SEQ ID NO 23
<211> LENGTH: 5
<212> TYPE: PRT
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-(5-pyrimidine) phenylalanine

<400> SEQUENCE: 23

Lys Leu Val Xaa Phe
1               5

<210> SEQ ID NO 24
<211> LENGTH: 5
<212> TYPE: PRT
```

```
<213> ORGANISM: Artificial sequence
<220> FEATURE:
<223> OTHER INFORMATION: cyclopeptide
<220> FEATURE:
<221> NAME/KEY: misc_feature
<222> LOCATION: (4)..(4)
<223> OTHER INFORMATION: Xaa is 4-(3-hydroxyphenyl) phenylalanine

<400> SEQUENCE: 24

Lys Leu Val Xaa Phe
1               5
```